United States Patent
Stelzer et al.

(10) Patent No.: US 6,187,953 B1
(45) Date of Patent: Feb. 13, 2001

(54) GUANIDINIUM PHOSPHANES, THEIR PRODUCTION AND THEIR USE

(75) Inventors: Othmar Stelzer, Wuppertal; Franz Peter Schmidtchen, Eching; Antonella Hessler; Michael Tepper, both of Wuppertal; Harald Dibowski, Eching, all of (DE); Michael Riedel, Bay City, TX (US); Helmut Bahrmann, Hamminkeln (DE)

(73) Assignee: Celanese GmbH (DE)

( * ) Notice: Under 35 U.S.C. 154(b), the term of this patent shall be extended for 0 days.

(21) Appl. No.: 09/341,834
(22) PCT Filed: Jan. 14, 1998
(86) PCT No.: PCT/EP98/00181
  § 371 Date: Nov. 17, 1999
  § 102(e) Date: Nov. 17, 1999
(87) PCT Pub. No.: WO98/31694
  PCT Pub. Date: Jul. 23, 1998

(30) Foreign Application Priority Data

Jan. 16, 1997 (DE) .............................. 197 01 245

(51) Int. Cl.⁷ ....................................... C07F 9/50
(52) U.S. Cl. ................ 564/15; 564/230; 568/17
(58) Field of Search .......... 564/15, 230; 568/8, 568/17

(56) References Cited

U.S. PATENT DOCUMENTS 5,057,618   10/1991   Herrmann et al. .
5,155,274   10/1992   Herrmann et al. .

FOREIGN PATENT DOCUMENTS 3840600   6/1990   (DE) .

OTHER PUBLICATIONS

1997 American Chemical Society, Hessler et al p. 2362–2369 Tetrahedron, vol. 51, No. 8, pp. 2325–2330, 1995 Dibowski et al.

*Primary Examiner*—Jean F Vollano
(74) *Attorney, Agent, or Firm*—Bierman, Muserlian and Lucas

(57) ABSTRACT

Guanidinium phosphanes of Formula I

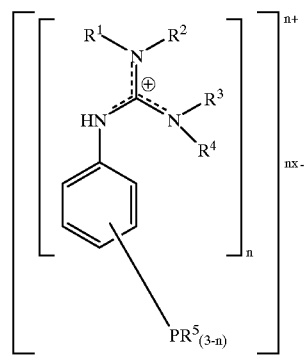

wherein the substituents are defined as in the specification which are useful catalyst ligands for the carbon-carbon linkage reactions of the hect reaction.

9 Claims, No Drawings

GUANIDINIUM PHOSPHANES, THEIR PRODUCTION AND THEIR USE

This is the national phase of PCT/EP98/00181, filed Jan. 14, 1998, now WO 98/31694.

The invention relates to guanidinium phosphines, a process for preparing them and their use.

For many reactions in the chemical industry, water is of great interest as solvent. However, organic reactions frequently have the disadvantage that they do not proceed or proceed to only an unsatisfactory extent in aqueous systems. However, complexes such as the trisodium salt of tris(m-sulfophenyl)phosphine make it possible to prepare catalyst systems which are employed in the hydroformylation of olefins (DE-A-38 40 600).

Compared to other known catalysts which are used for the abovementioned reaction, they have the advantage of being soluble in water. The hydroformylation can therefore by carried out in a heterogeneous reaction medium consisting of an aqueous phase and an organic phase (two-phase system), as is described in DE-A-38 40 600.

The advantage of such a process is that the final product can be separated from the water-soluble catalyst by simple phase separation. Furthermore, the noble metal catalyst can be recovered virtually without losses in this way or can be recirculated to the synthesis step (DE-A-26 27 354).

To prepare water-soluble catalyst systems, phosphorus-containing compounds are of particular interest. Examples are catalysts comprising palladium complexes containing anionic phosphines as ligands.

Cationic phosphine-containing ligands have been little studied in the past, although they should likewise have a favorable effect on the abovementioned reactions.

This object is achieved by guanidinium phosphines of the formula I,

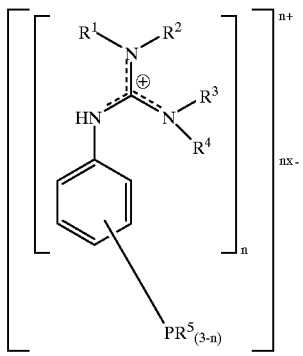

I where n is an integer from 1 to 3,

X is Cl, Br, I or $PF_6$, $R^1$ and $R^2$ are hydrogen and $R^3$ and $R^4$ are methyl or $R^1$ and $R^2$ are methyl and $R^3$ and $R^4$ are hydrogen and $R^5$ is a phenyl group and the guanidinium substituent is located in the meta or para position relative to the P atom.

The object is likewise achieved by guanidinium phosphines of the general formula II

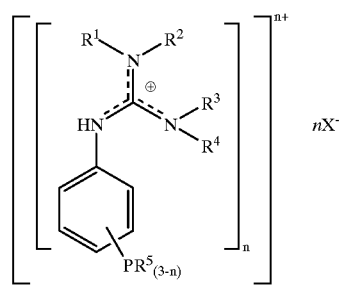

II where n is 1 or 2,

X is Cl, Br, I or $PF_6$, $R^1$, $R^2$, $R^3$, $R^4$ are identical or different and are each a $C_1$–$C_6$-alkyl group or hydrogen, with the exception of $R^1$ and $R^2$ being hydrogen and $R^3$ and $R^4$ being methyl or $R^1$ and $R^2$ being methyl and $R^3$ and $R^4$ being hydrogen, and $R^5$ is a phenyl group and the guanidinium substituent is located in the meta or para position relative to the P atom.

The invention likewise provides a process for preparing guanidinium phosphines of the general formula I, which comprises reacting N-aminophenylphosphines of the formula III,

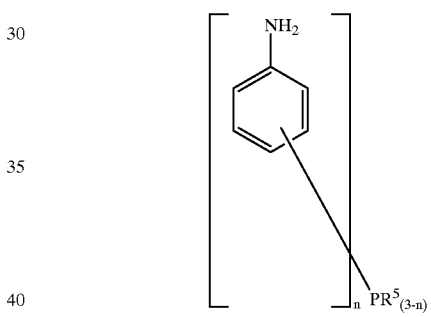

III where n and $R^5$ are as defined in formula I, with dimethyl-cyanamide to give guanidinium phosphines of the formula I. The preparation of N-aminophenylphosphines is known, for example, from J. Organomet. Chem. 1996, 522, 69, Phosphorus 1997, 1, 187 or from Chem. Ber. 1971, 104, 1722.

Preferably, the N-aminophenylphosphines of the formula III are first reacted with equimolar amounts of a solution of HCl in ether or water to form the HCl adducts of the formula IV,

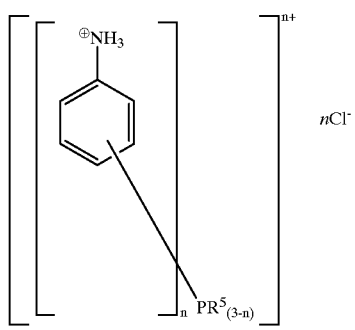

IV where n and $R^5$ are as defined in formula I, and the reaction step with the dimethylcyandiamide is then carried out.

The invention likewise provides a process for preparing guanidinium phosphines of the formula I, with the exception of n=3, or II, which comprises reacting primary and secondary phosphines $R^5{}_{3-n}PH_n$ (n=1 or 2) with meta- or para-iodophenylguanidines of the formula V,

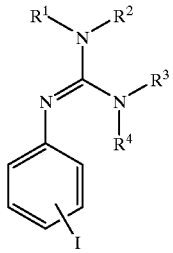

formula V where

R$^1$, R$^2$, R$^3$, R$^4$ are as defined in formula I or II and the iodine atom is located in the meta or para position relative to the guanidine group. C. Ferri, Reaktionen der organischen Synthese, Georg Thieme Verlag, Stuttgart, 1978, Synthesis 1988, 460 and Y. Yamomoto, S. Kojima, The Chemistry of Amidines and Imidates, vol. 2, edited by S. Patai, Z. Rappoport, John Wiley & Sons, New York 1991, page 491, disclose that alkyl-substituted cyanamides can be reacted with amines or substituted anilines to give substituted guanidines.

Preference is given to using acetonitrile, dimethylacetamide, ether and/or hydrocarbons as solvents.

As catalysts for this reaction, preference is given to using palladium(II) acetate, palladium(II) halidephosphine complexes, palladium(0)-olefin complexes, palladium(0)-phosphine complexes and finely divided metallic palladium.

The invention likewise provides for the use of the compounds of the formula I or II for preparing catalyst ligands for carbon-carbon linkage reactions.

The invention is illustrated by the following examples in which the compounds of the invention are prepared in the form of their chlorides, bromides, iodides and hexafluorophosphates.

EXAMPLE 1

3.5 ml of a solution of HCl in ether (1.65 N) are added while stirring to a solution of 2.25 g (8.1 mmol) of diphenyl (3-aminophenyl)phosphine in 20 ml of dichloromethane. The solvent is distilled off and the residue is crystallized by addition of a small amount of diethyl ether and subsequently dried under reduced pressure.

This gives 2.48 g of diphenyl(3-ammoniumphenyl)phosphine chloride corresponding to a yield of 98%.

The abovementioned product (2.48 g; 7.9 mmol) is added to an excess of dimethylcyanamide (2.90 g; 41.1 mmol) and stirred at 110° C. for 12 hours. To remove the excess of dimethylcyanamide, the highly viscous reaction mixture is extracted with 30 ml of ether, giving 2.78 g of diphenyl(3-(N,N-dimethylguanidinium)phenyl)phosphine chloride as a cream-colored solid (yield: 92%).

EXAMPLE 2

5.1 ml of a solution of HCl in ether (1.65 N) are added while stirring to a solution of 1.26 g (4.3 mmol) of phenylbis (3-aminophenyl)phosphine in 20 ml of tetrahydrofuran. 1.53 g of phenylbis(3-ammoniophenyl)phosphine dichloride is precipitated as a white product (yield: 97%).

The abovementioned product (1.53 g; 4.2 mmol) is added to an excess of dimethylcyanamide (1.20 g; 17.1 mmol) and stirred at 110° C. for 4 hours. To remove the excess of dimethylcyanamide, the highly viscous reaction mixture is extracted with 30 ml of ether, giving 1.96 g of phenylbis(3-(N,N-dimethylguanidino)phenyl)phosphine dichloride as a cream-colored solid (yield: 92%).

EXAMPLE 3

An aqueous solution of 3.04 g (9.90 mmol) of tris(3-aminophenyl)phosphine in 100 ml of water was treated with 13.5 ml of hydrochloric acid (2 N) and the clear solution was stirred at room temperature for 30 minutes. The solvent was distilled off at 60° C. under reduced pressure, giving 3.21 g of tris(3-ammoniophenyl)phosphine trichloride as a colorless solid (yield: 78%).

The abovementioned product (1.90 g; 4.6 mmol) is added to an excess of dimethylcyanamide (4.36 g; 62.2 mmol) and stirred at 110° C. for 12 hours. To remove the excess of dimethylcyanamide, the highly viscous reaction mixture is extracted with 30 ml of ether, giving 2.79 g of tris[3-(N,N-dimethylguanidinium)phenyl]phosphine trichloride as a cream-colored solid (yield 97%).

EXAMPLE 4

46.00 g (0.21 mol) of 3-iodoaniline were admixed with 100 ml of 15% strength hydrochloric acid. The 3-iodoanilinium hydrochloride formed was filtered off with suction, recrystallized from water and dried under reduced pressure (yield: 52.57 g=98%). The total amount of the anilinium salt was mixed with 14.42 g (0.205 mol) of dimethylcyanamide and heated at 130° C. for 10 minutes on an oil bath. After the reaction had abated, the reaction mixture was cooled, admixed with 100 ml of water and the water-soluble constituents were filtered off. The aqueous solution was extracted twice with 100 ml each time of diethyl ether, adjusted to a pH of 10–12 using KOH and subsequently extracted three times with 100 ml of dichloromethane. The CH$_2$Cl$_2$ extracts were dried over magnesium sulfate and the solvent was then taken off under reduced pressure. This left 48.2 g of N'-(3-iodophenyl)-N,N-dimethylguanidine as a colorless solid (yield: 81%).

A solution of the abovementioned product (32.10 g; 0.111 mol) and 6.16 g (0.056 mol) of PhPH$_2$ in 150 ml of acetonitrile was carefully degassed and saturated with nitrogen and, while stirring vigorously, 0.25 g (0.22 mmol) of Pd(Ph$_3$P)$_4$ (0.2 mol %) was then added. The reaction mixture was heated under reflux for 40 hours and the solvent was subsequently taken off under reduced pressure (20° C., 0.2 mbar). This left 37.6 g of phenylbis(N,N'-dimethylguanidinium)phenylphosphine diiodide as a cream-colored residue (yield: 97%).

EXAMPLE 5

20.0 g of 4-iodoaniline hydrochloride (78.3 mmol) and 3.29 g (78.3 mmol) of cyanamide were finely milled and intimately mixed with one another. The mixture was melted at 140° C. and held at this temperature for about 3 minutes. The mixture foams and darkens and the guanidinium salt [4-I—C$_6$H$_4$—NH—C(NH$_2$)$_2$]Cl is formed. The black melt cake was cooled and then taken up in 200 ml of hot (about 80° C.) water and the solution obtained was extracted five times with 50 ml each time of ether. The aqueous Guanidinium phosphines, a process for preparing them and their use.

What is claimed is:

1. A compound o the formula

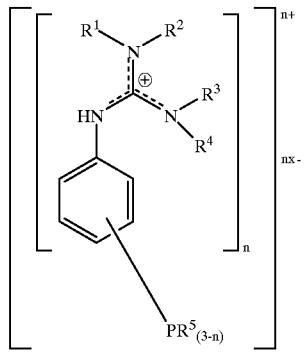

wherein n is an integer of 1 to 3, X is selected from the group consisting of chlorine, bromine, iodine and $PF_6$, $R^1$ and $R^2$, are hydrogen and $R^3$ and $R^4$ are methyl or $R^1$ and $R^2$ are methyl and $R^3$ and $R^4$ are hydrogen, $R^5$ is phenyl and the guanidinium is located meta or para with respect to the phosphorus atom.

2. A compound of the formula

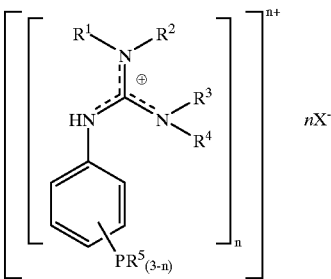

wherein n is 1 or 2, X is selected from the group consisting of chlorine, bromine, iodine and $PF_6$, $R^1$, $R^2$, $R^3$ and $R^4$ are individually hydrogen or alkyl of 1 to 6 carbon atoms with the proviso that $R^1$ and $R^2$ are not hydrogen when $R^3$ and $R^4$ are methyl or $R^1$ and $R^2$ are not methyl when $R^3$ and $R^4$ are hydrogen, $R^5$ is phenyl and the quanidinium is meta or para with respect to the phosphorus atom.

3. A process for the preparation of a compound of claim 1 comprising reacting a compound of the formula

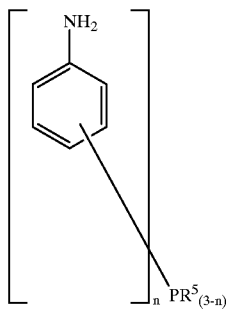

wherein n and $R^5$ are defined as in claim 1 with dimethylcyamide to form the compound of claim 1.

4. The process of claim 3 wherein the compound of Formula III is first reacted with an equimolar amount of hydrochloric acid in solution in ether or water to form the HCl adduct of the formula

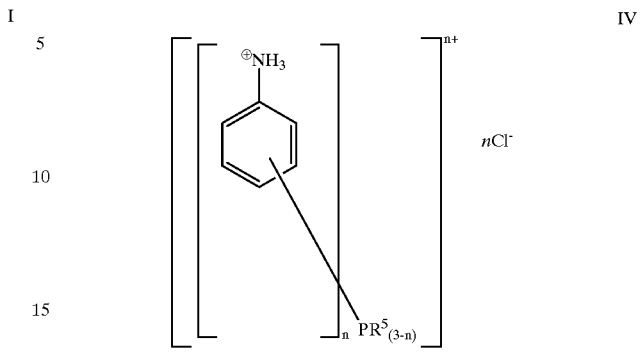

which is then reacted with dimethylcyamide.

5. A process for the preparation of a compound of claim 1 wherein n is not 3 comprising reacting a phosphine of the formula $R^5_3PH_n$ wherein n is 1 or 2 with a meta- or para-iodophenyl guanidinium of the formula

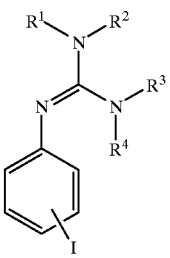

wherein $R^1$, $R^2$, $R^3$, $R^4$ and $R^5$ are defined as in claim 1 and the iodine is meta- or para-position with respect to the quanidinium.

6. A process for the preparation of a compound of claim 2 comprising reacting a phosphine of the formula $R^5_3PH_n$ wherein n is 1 or 2 and $R^5$ is defined as in claim 2 with a meta- or para-iodophenyl guanidinium of the formula

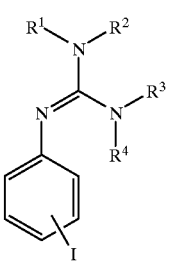

wherein $R^1$, $R^2$, $R^3$ and $R^4$ are as defined as in claim 2 and the iodine is meta- or para- to the guanidinium.

7. The process of claim 5 wherein the reaction is carried out in at least one solvent selected from the group consisting of acetonitrile, dimethylacetamide, ether and hydrocarbons.

8. The process of claim 5 wherein the reaction uses a catalyst selected from the group consisting of palladium (II) acetate, a palladium (II) halide phosphine complex, a palladium (0)-phosphine complex and finely divided palladium.

9. The process of claim 6 wherein the reaction uses a catalyst selected from the group consisting of palladium (II) acetate, a palladium (II) halide phosphine complex, a palladium (0)-phosphine complex and finely divided palladium.

* * * * *